United States Patent [19]

Mallinson et al.

[11] Patent Number: 5,212,067

[45] Date of Patent: May 18, 1993

[54] QUICK ASSAY FOR DETECTION OF SALMONELLA

[75] Inventors: Edward T. Mallinson, Columbia; Christopher R. Tate, Frederick; Russell G. Miller, Glen Dale, all of Md.

[73] Assignees: The United States of America as represented by the Secretary of Agriculture, Washington, D.C.; The University of Maryland, College Park, Md.

[21] Appl. No.: 330,479

[22] Filed: Mar. 30, 1989

[51] Int. Cl.$^5$ ............ C12Q 1/10; C12Q 1/02; C12Q 1/24; C12Q 1/22

[52] U.S. Cl. ................... 435/38; 435/29; 435/30; 435/31; 435/34; 435/39; 435/295

[58] Field of Search ........... 435/295, 29, 30, 31, 435/34, 38, 39, 295

[56] References Cited

U.S. PATENT DOCUMENTS

| | | | |
|---|---|---|---|
| 2,034,986 | 3/1936 | Mislowitzer | 435/295 |
| 3,163,160 | 12/1964 | Cohen | 435/295 |
| 3,308,039 | 3/1967 | Nelson | 435/295 |
| 4,184,483 | 1/1980 | Greenspan | 435/295 |
| 4,223,093 | 9/1980 | Newman et al. | 435/295 |
| 4,312,950 | 1/1982 | Snyder et al. | 435/295 |
| 4,770,853 | 9/1988 | Bernstein | 422/58 |

OTHER PUBLICATIONS

Fisher Scientific Catalogue 1988, pp. 1521 & 1520 & 1458.
Difco Manual, 10th Edition 1984, pp. 947-949.
Julseth et al. (1964) Effect of temperature on—Appl. Microbiol 17:767-768.
Dega et al. (1972) Growth of Salmonella—Appl. Microbiol 23:82-87.

Primary Examiner—Christine M. Nucker
Assistant Examiner—David R. Preston
Attorney, Agent, or Firm—Oblon, Spivak, McClelland, Maier & Neustadt

[57] ABSTRACT

A swift, accurate assay for the detection of salmonella contamination in a livestock environments, comprises sampling the floor of the livestock holding area with drag swabs for about 10 or more minutes, after which said swabs are maintained in a static condition, at reduced temperature, in the presence of double strength skim milk, until ready for testing. The swabs are transferred to a salmonella-preferential growth medium, such as tetrathionate broth and subsequently assayed. To reduce non-salmonella "look alike" or masking bacterial colonies, Novobiocin may be administered to the culture media.

7 Claims, No Drawings

QUICK ASSAY FOR DETECTION OF SALMONELLA

FIELD OF THE INVENTION

A fast, accurate, low cost and low labor-intensive assay for the detection of salmonella infection or contamination in livestock farms, especially poultry houses is provided.

BACKGROUND OF THE PRIOR ART

Salmonella bacteria have been implicated as the source of food poisoning, gastrointestinal infection, and generalized (septicemic) infection, that can become quite severe and even lethal in humans and livestock. A common source of salmonella infection is from the food supply, particularly livestock-derived food, such as poultry, as well as other farm-raised animals, such as cattle, swine, and sheep. Poultry farms and other livestock operations are continually at risk of salmonella infection, with subsequent survival and multiplication. These bacteria are potentially infectious to humans. Accordingly, the early detection of salmonella contamination or infection on these livestock farms, prior to delivery of contaminated food to processing plants and subsequently to the marketplace, is a primary concern of the livestock industry and governmental regulating and research agencies.

Currently salmonella sampling methods involve the direct collection of feathers, feces and other animal traces, a time and labor consuming process, which samples, must then be cultured, plated, and grown, and biochemically analyzed, constituting a process which can consume up to 14 days, before complete results are obtained. Clearly, a faster test, with equal reliability, which is not excessively labor intensive or costly is necessary to prevent eventual delivery of contaminated food stuffs to the marketplace by prior detection of the infection or potential infection. Provision of faster turn-around time in the laboratory provides for faster testing of a greater number of samples, which is needed for industry-grade (extensive) monitoring prior to slaughter, or other forms of in house or regulatory quality control. To date, current sampling, culturing and plating methods take too long, and frequently give rise to problems in distinguishing salmonella bacteria from other related non-toxic bacterial cultures. It would also be desirable to provide a method which gives some indication of the animals' condition prior to sacrifice.

SUMMARY OF THE INVENTION

The above objectives and other objectives more clearly set forth below, are achieved through an assay process that consumes, in total, as little as 24-30 hours, for positive detection of salmonella infection. Alternatively, the assay provides a holding media which can provide for collection of a large number of samples for a period up to 2 weeks, and then simultaneous assay of all collected samples, so that automation or routinization of the process is easily achieved, to reduce cost, without a sacrifice of accuracy or essential speed.

Rather than piece collection of physical samples, a drag swab is employed, i.e., strips, pads or other lengths of moistened gauze or fabric swabs are dragged along the floor of the poultry or livestock house, during the caretakers' routine duties. Over a short period, e.g., 10-20 minute time period, sufficient sampling is achieved, to ensure reliable detection of any salmonella infection present.

The swabs are held, in static condition, in a holding media comprised of skim milk, preferably double strength, at reduced temperature. It should be noted that the swabs themselves may be preimpregnated with the holding media, and freeze dried or otherwise preserved for long storage. If freeze dried, the swab can be "activated" by moistening. On receipt, the swabs are transferred to a culture broth preferential for the growth of salmonella. The inventors have determined that conventionally known Hajna TT broth (a formulation of tetrathionate broth) preferentially promotes the growth of salmonella cultures.

After a relatively quick growth stage in the culture broth, about 20 hours, the broth may be assayed within about 2 directly, for the presence of salmonella cultures. A suitable assay is an enzyme immunosorbent assay, or ELISA. Other assays such as radioimmunoassays are familiar to those of skill in the art. Problems with the presence of bacteria that resemble or mask the presence of salmonella, but are not in fact salmonella or non-infectious, but frustrate visual inspection assays, can be further suppressed by the addition of an antibiotic, Novobiocin, which suppresses the growth of these contaminating, competing bacteria. The impact of Novobiocin in suppressing competitive growth is more clearly obtained by plating out the culture broth onto salmonella-preferential media, supplemented with the antibiotic. A short growth period, of no more than about 2 days is ordinarily sufficient to provide information to confirm or dismiss the culture as a salmonella contamination.

DETAILED DESCRIPTION OF THE INVENTION

In order to reduce the time, labor and logistic factors involved in achieving positive confirmation of salmonella infection or contamination on a farm, the time-consuming sampling system of tissue samples, such as feathers from poultry and the like, and other samples, such as feces, must be avoided. A suitable alternative, documented in the literature as providing equivalent, complete, representative sampling of the contamination present, is the drag swab method, wherein a plurality of small strips of wet gauze swabs, pads, etc. are dragged along the floor of the livestock house, such as the chicken coop or house, barn, etc. Such a sampling method is complete, and gives results comparable to the tissue sampling common in the industry, as confirmed by Kingston, *Avian Diseases*, 25:513-516, 1981 and the inventors (to be reported in Avian Diseases). Conveniently, the swabs can be dragged on the ground by the caretaker, behind him during normal activities, and simply collected following the conclusion of those activities, and maintained in a static condition, until the sample can be shipped, and assayed.

Quite surprisingly, a preferred medium for maintaining the bacterial growth conditions of the sample static is skim milk (milk from which substantially all the fat has been removed) preferably double strength. Drag swabs, held in the skim milk preparation at a temperature at below about 10° C, e.g., 0°-10° C. preferably about 4° C., have been demonstrated to maintain the drag swabs nearly entirely static, such that no loss of bacteria present in the sample, or over representation is observed. As noted, a particularly useful drag swab is preimpregnated with the holding media, in a stabilized form, such as freeze dried.

When a sufficient number of samples has been collected, over a time less than 2 weeks, the swabs are taken from the skim milk holding medium, and transferred into a culture broth that is preferential for salmonella growth. Thus shipment of batched samples over great distances to remote laboratories under simple refrigeration, for testing on mass is possible. Suitable broths comprise tetrathionate, and are commercially available. Thus, the Hajna tetrathionate selective enrichment broth, or traditional Muller-Kauffman tetrathionate broth, both available from Difco and Becton-Dickinson are suitable as preferential growth media. The Hajna broth is available under the mark BACTO-TT broth base, product code number 0491-01-5. Another tetrathionate broth, such as the Muller-Kauffman formulation, can be substituted, with slightly inferior results. Notwithstanding the preferential nature of the culture broth, other bacterial growths, facially similar to salmonella growths, may be encouraged. These "look alikes" or "suspicious" cultures can be further suppressed by the use of the antibiotic Novobiocin, also commercially available from Sigma, St. Louis. The range of concentration in the broth varies but about 20 micrograms per ml of broth appear to be an optimal value. Concentration ranges may run from 1 microgram per ml up to 50 micrograms per ml, preferably 15-20 $\mu g/ml$, depending on the results desired, and the sensitivity of the study to be employed.

Growth of "look alike" non-salmonella or overgrowth of salmonella masking bacterial colonies can be further suppressed by plating the culture broth onto traditional preferential growth media, such as xylose-lysine-deoxycholate (XLD) and plain brilliant green (BG) agar growth media supplemented with Novobiocin, in the aforementioned concentration range. This supplementation suppresses mainly bacteria which would otherwise interfere with the detection of salmonella, thus making the culture media markedly more reliable in establishing the true salmonella status of the sample.

The samples collected can be assayed, either directly from the culture broth by a rapid assay or subjected to visual analysis on Novobiocin supplemented BG or XLD plates, requiring an additional 24-48 hours. Although any of a variety of commercially available rapid assays may be used, ELISA assays provide high sensitivity, with a relatively rapid assay protocol. A particularly preferred assay is an antigen capture ELISA, conducted under conventional protocol, that is, an assay which employs a bound antibody, monoclonal or polyclonal, to bind to the antigen in question. After washing any portion of the analite not bound away, the test plate or support is exposed to a second antibody, which is complexed with a marker of some type, usually a chromophore. The presence of antigen in the sample is determined by detecting the chromophore, as through an optical density reader, as the chromophore is released when the antibody binds to the antigen. On antigen capture ELISA is available from Kirkegaard and Perry Laboratories, Gaithersburg, Maryland. The entire assay takes approximately 2-4 hours.

Thus, once adequate samples are recovered, if the sample is cultured in a preferential broth, and tested directly therefrom, positive results can be obtained in about 24-30 hours. The method is neither labor intensive, nor does it require specialized or adapted machinery. Given the ability of the static holding media to maintain bacteria profiles over a period of time up to 2 weeks, thus increasing the number of samples submitted, automation is quite straightforward.

It should be noted that the same assay process enables the determination of the collective state of the farms' animals, without or prior to sacrifice of the animals. Salmonella presence in the drag swab virtually guarantees salmonella infection in at least some of the animals. This may sharply reduce contamination of food processing plants.

The above invention has been described with reference to specific embodiments, and generalized description. Clearly, alternatives will occur to those of skill in the art, such as varied culture mediums, broths, alternative temperature periods, etc., without departing from the scope of the invention, as set forth in the claims appended hereto.

What is claimed is:

1. A method for monitoring structures housing livestock for salmonella contamination, consisting essentially of:
    (A) periodically collecting drag swab samples, said drag swab samples having been dragged along the floor of said structure for at least 10-20 minutes,
    (B) maintaining said drag swabs for a period of up to two weeks in a holding medium consisting essentially of double strength skim milk, at a temperature below about 10° C.,
    (C) transferring said swabs to a culture broth which supports growth of salmonella cultures, and culturing said swabs for about 15-30 hours, at a temperature between about 35°-43° C., so as to promote the multiplication of any salmonella organisms captured in said drag swabs, and
    (D) qualitatively assaying said culture broth for the presence of salmonella cultures.

2. The process of claim 1, wherein said culture broths are plated onto salmonella preferential culture media, supplemented with Novobiocin in concentrations of 1-50 micrograms/ml, prior to said assay step.

3. The process of claim 1, wherein said assay is an antigen capture enzyme-linked immunosorbent assay.

4. The process of claim 1, wherein said culture broth is a tetrathionate-comprising broth.

5. A drag swab useful in the process of claim 1, comprising a length of fabric impregnated with liquid/skim milk, and subsequently stabilized by freeze drying.

6. The drag swab of claim 5, wherein said skim milk is double strength.

7. The method of claim 1, wherein said assaying step is also quantitative.

* * * * *